US007297505B2

(12) United States Patent
Rusinko et al.

(10) Patent No.: US 7,297,505 B2
(45) Date of Patent: Nov. 20, 2007

(54) USE OF MDCK CELL LINE TO PREDICT CORNEAL PENETRATION OF DRUGS

(75) Inventors: Andrew Rusinko, Arlington, TX (US); Mark R. Hellberg, Arlington, TX (US); Jesse Albert May, Fort Worth, TX (US); Geoffrey Robert Owen, Southlake, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/114,649

(22) Filed: Apr. 25, 2005

(65) Prior Publication Data

US 2005/0239050 A1     Oct. 27, 2005

Related U.S. Application Data

(60) Provisional application No. 60/564,790, filed on Apr. 23, 2004.

(51) Int. Cl.
   *G01N 33/567* (2006.01)
(52) U.S. Cl. .................. 435/7.21; 435/7.1; 435/32; 435/40.51
(58) Field of Classification Search ............. 435/7.1, 435/7.21, 32, 40.51
   See application file for complete search history.

(56) References Cited

U.S. PATENT DOCUMENTS

2003/0144336 A1   7/2003   Chen et al.
2003/0235580 A1   12/2003  Zhang

OTHER PUBLICATIONS

Dey S, et al. (2003) Molecular evidence and functional expression of P-glycoprotein (MDR1) in human rabbut cornea nad corneal epithelial cell lines. Investigative Ophthalmology and Visual Science vol. 44 No. 7: pp. 2909-2918.*
Guo A, et al. (2002) Delineating the contribution of secretory transporters in the efflux of etoposide using Madin-Darby canine kidney cells . . . Drug Metabolism and Disposition vol. 30 No. 4: pp. 457-463.*
Botham P, et al. (1997) IRAG working group 3: Cell function-based assays. Food and Chemical Toxicology vol. 35: pp. 67-77.*
Anand BS, Patel J, and Mitra AK (2003) Interactions of the Dipeptide Ester Produrgs of Acyclovir with the intestinal oligopeptide transporter: competitive inhibition of glycylsarcosine transport in human intestinal cell line Caco-2. J Pharmacol Exp Therapeut 304: pp. 781-791.*
Putnam WS, Pan L, Tsutsui K, Takahashi L, Benet LZ (2002) Comparison of bidirectional transport across MDCK and Caco-2 cell monolayers: interactions with peptide transporters. Pharmaceut Res 19: pp. 27-33.*
Shen, et al., "Evaluation of an Immortalized Retinal Endothelial Clel Line as an in Vitro Model for Drug Transport Studies Across the Blood-Retinal Barrier"; *Pharmaceutical Research*; vol. 20, No. 9, pp. 1357-1363 (2003).

Edwards, et al., "Predicted Permeability of the Corneal to Topical Drugs", *Pharmaceutical Research*; vol. 18, No. 1; pp. 1497-1508.
Malhotra, et al., "Permeation through Cornea", *Indian Journal of Experimental Biology*, vol. 39, pp. 11-24; Jan. 2001.
Sasaki, et al., "Intestinal Permeability of Ophthamlic B-Blockers for Predicting Ocular Permeability", *Journal of Pharmaceutical Sciences*; vol. 83, No. 9; pp. 1335-1338; (Sep. 1994).
Ranta, et al., "Ocular Pharmacokinetic Modeling Using Corneal Absorptin and Desorption Rates from in Vitro Permeating Experiments with Cultured Corneal Epithelial Cells", *Pharmaceutical Research*, vol. 20, No. 9, pp. 1409-1416 (Sep. 2003).
Yoshida, et al., "Unified Model for the Corneal Permeability of Related and Diverse Compounds with Respect to Their Physicochemical Properties", *Journal of Pharmaceutical Sciences*, vol. 85, No. 8, pp. 819-823; (Aug. 1996).
Wang, et al., "Lipophilicity Influence on Conjunctival Drug Penetration in the Pigmented Rabbit: A Comparison with Corneal Penetration", *Current Eye Research*, vol. 10, No. 6, pp. 571-579, (1991).
Liu, et al., "Pharmacokinetics of Sparfloxacin in the Serum and Vitreous Humor of Rabbits: Physicochemical Properties That Regulate Penetration of Quinolone Antimicrobials", *Antimicrobial Agents and Chemotherapy*, vol. 42, No. 6, pp. 1417-1423; (Jun. 1998).
Prausnitz, et al., "Permeability of Cornea, Sclera, and Conjuctiva: A Literature Analysis for Drug Delivery to the Eye", *Journal of Pharmaceutical Sciences*, vol. 87, No. 12, pp. 1479-1488; (Dec. 1998).
Fukuda, et al., "In Vitro Topically Applied Fluoroquinolone Penetration into the Anterior Chamber", *Journal of the Japanese Ophthalmic Society*, vol. 99, pp. 532-536, (1995).
Viswanadhan, et al., "Atomic Physicochemical Parameters for Three Dimensional Structure Directed Quantative Structure-Activity Relationshps", *J. Chem. Inf. Computer Science*, vol. 29, pp. 163-172 (1989).
Kowalski, et al., "Gatifloxacin and Moxifloxacin: An In Vitro Susceptibility Comparison to Levofloxacin, Ciprofloxacin, and Ofloxacin Using Bacterial Keratitis Isolates", *American Journal of Opthalmology*, vol. 136, No. 3, pp. 500-505; (Sep. 2003).
Mather, et al., "Fourth Generation Fluoroquinolones: New Weapons in the Arsenal of Ophthalmic Antibiotics"; *American Journal of Ophthalmology*, vol. 133, No. 4, pp. 463-466, (Apr. 2002).
Pestova, et al., "Intracellular Targets of Moxifloxacin: a Comparison With Other Fluoroquinolones", *British Society of Antimicrobial Chemotherapy*, vol. 45, pp. 583-590; (2000).

(Continued)

*Primary Examiner*—Ralph Gitomer
*Assistant Examiner*—Clark Petersen
(74) *Attorney, Agent, or Firm*—Mark E. Flanigan

(57) ABSTRACT

A new method of evaluating the ability of drug molecules to penetrate the cornea is described. The permeation rate of the drug molecules in MDCK cells is utilized to predict the ability of the molecules to penetrate the cornea. The method is useful for in vitro screening of potential new ophthalmic drugs, as well as in the design of new drug molecules for topical ocular administration.

3 Claims, 2 Drawing Sheets

OTHER PUBLICATIONS

Jester, et al., "Area and Depth of Surfactant-Induced Corneal Injury Predicts Extent of Subsequent Ocular Responses", *Investigative Ophthalmology & Visual Science*, vol. 39, No. 13, pp. 2610-2625, (Dec. 1998).

Horio, et al., "Transepithelial Transport of Vinblastine by Kidney-Derived Cell Lines. Application of a New Kinetic Model to Estimate in situ $K_m$ of the Pump", *Biochimica et Biophysica Acta*, pp. 116-122, (1990).

Pan, et al., "Enhanced Transepithelial Flux of Cimetidine by Madin-Darby Canine Kidney Cells Overexpressiing Human P-Glycoprotein", *Journal of Pharmacology and Experiemental Therapeutics*, vol. 270, No. 1, pp. 1-7, (1994).

Arimori, et al., "Effect of P-Glycoprotein Modulator, Cyclosporin A, on the Gastrointestinal Excretion of Irinotecan and its Metabolite SN-38 in Rats", *Pharmaceutical Research*, vol. 20, No. 6, pp. 910-916.

Lee, et al., "Improved Ocular Drug Delivery With Prodrugs in Prodrugs", *Topical and Ocular Drug Delivery*, Sloan, K.B., (ed.), pp. 221-297, Marcel Dekker, NY, NY, (1992).

Schoenwald, et al., "Relationshp Between Steroid Permeability Across Excised Rabbit Cornea and Octanol-Water Partition Coefficients" *Journal of Pharmaceutical Sciences*, vol. 67, No. 6, pp. 786-788; (Jun. 1978).

Schoenwald, et al. "Corneal Penetration Behavior of B-Blocking Agents I: Physicochemical Factors", *Jounral of Pharmaceutical Sciences*, vol. 72, No. 11, (Nov. 1983).

Wu, et al, "In-Vitro Corneal Permeability of Cephalosporins", *The Chinese Pharmaceutical Journal*, vol. 43, No. 3, pp. 229-235, (Feb. 1991).

Ruiz-Garcia, et al., "Biophysical Models in Drug Development: 6-Fluoroquinolone Derivatives", *Proceedingsd of the International Symposium on Controlled Release of Bioactive Materials*, 27$^{th}$ Edition, pp. 708, (2000).

Mariscal, et al., "Tight Junction Formation in Cultured Epithelial Cells (MDCK)", *Journal of Membrane Biology*, vol. 86, pp. 113-125, (1985).

Fu, et al., "Prediction of Corneal Permeability Using Polar Molecular Surface Areas", *Pharmazie*, vol. 56, No. 8, p. 667, (2001).

Fu, et al., "A Simple Model for the Prediction of Corneal Pemeability", *International Journal of Pharmaceutics*, vol. 232, pp. 193-197, (2002).

Clark, "Rapid Calculation of Polar Molecular Surface Area and Its Application to the Prediction of Transport Phenomea. 1. Prediction of Intestinal Absorption", *journal of Pharmaceutical Sciences*, vol. 88, No. 8, pp. 807-814, (Aug. 1999).

Toropainen, et al., "Paracellular and Passive Transcellular Permeability in Immortalized Human Corneal Epithelial Cell Culture Model", *European Journal of Pharmaceutical Sciences*, vol. 20, pp. 99-106; (2003).

Romanowski, et al., "The in vitro e valuation of the ophthalmic fluoroquinolones against bacterial conjunctivities isolates", *Presented at the Ocular Microbiology and Immunology Group Meeting*, Anaheim, CA, Nov. 15, 2003, Abstract 1.

Caballero, et al., "Effectiveness of fluoroquinolone antibiotics for experimental mycobacterium chelonae keratitis", *Presented at the Ocular Microbiology and Immunology Group Meeting*, Anaheim, CA, Nov. 15, 2003, Abstract 22.

Katz, et al., "Human aqueous humor penetration pharmacokinetics of moxifloxacin afte topical administration of moxifloxacin 0.5% ophthalmic solution", *Presented at the Ocular Microbiology and Immulology Group Meeting*, Anaheim, CA, Nov. 15, 2003, Abstract 10.

Kim, et al., "Evaluation of the effects of topical ophthalmic fluoroquinolones (FQ) on the cornea using in vivo confocal microscopy", *Invest. Ophthalmol Vis. Science (ARVO)*, 2003 Abstracts vol. 1, #1367, May 4-9, 2003.

Robertson, et al., "Penetration and distribution of moxifloxacin and ofloxacin into ocular tissues and plasma following topical ocular administration to pigmented rabbits", *Invest. Ophthalmol Vis. Science (ARVO)*, 2003 Abstracts vol. 1, #1454, May 4-9, 2003.

Singh et al., "Ocular delivery screening scheme for systemically administered ophthalmic drugs", *Invest. Ophthalmol Vis. Science (ARVO)*, 2003 Abstracts vol. 2, #4426, May 4-9, 2003.

Owen, et al., "Corneal penetration and changes in corneal permeability of moxifloxacin versus gatifloxacin", *Invest. Ophthalmol. Vis. Science (ARVO)*, 2004 Abstract #4910 [obtained on line at www.arvo.org].

Rusinko, et al. "A study of the enhanced corneal penetration of moxifloxacin", *Invest. Ophthalmol. Vis. Science (ARVO)*, 2004, Abstract #4907 [obtained on line at www.arvo.org].

Gautheron, et al., "Investigations of the MDCK permeability assay as an in vitro test of ocular irritancy", *In Vitro Toxicology*, vol. 7, No. 1, pp. 33-43, 1994.

Goskonda et al., Permeability Characteristics of Novel Mydriatic Agents Using an in Vitro Cell Culture Model that Utilizes Sirc Rabbit Corneal Cells, J Pharma Sciences, 1999, vol. 88(2):180-184.

Irvine et al., MDCK (Madlin-Darby Canine Kidney) Cells: A Tool for Membrane Permeabilty Screening, J Pharma Sciences, 1999, vol. 88(1):28-33.

Lavelle et al., Low Permeabilities of MDCK Cell Monolayers: A Model Barrier Epithelium, American J Physiology, 1997, vol. 273(1)2:F67-F75.

Robertson et al., Ocular Pharmacokinetics of Moxifloxacin after Topical Treatment of Animals and Humans, Survey of Ophthalmology, 2005, vol. 50(1):S32-S45.

* cited by examiner

Figure 1. Factors influencing penetration of the corneal epithelium.
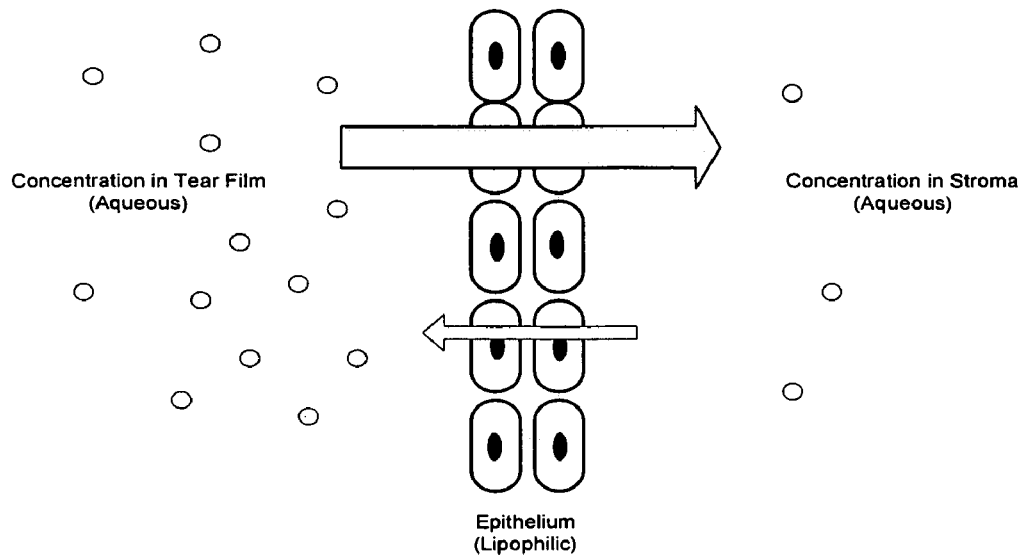
A. Concentration gradient favors greater aqueous solubility
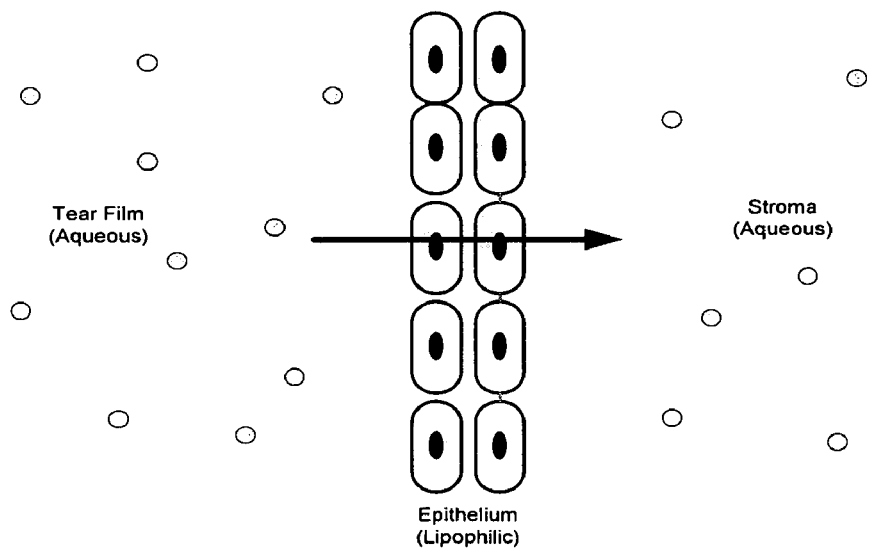
B. Higher lipophilicity results in greater transcellular permeability Figure 2. MDCK cell permeability rate correlates well with corneal permeability rates for fluoroquinolones.
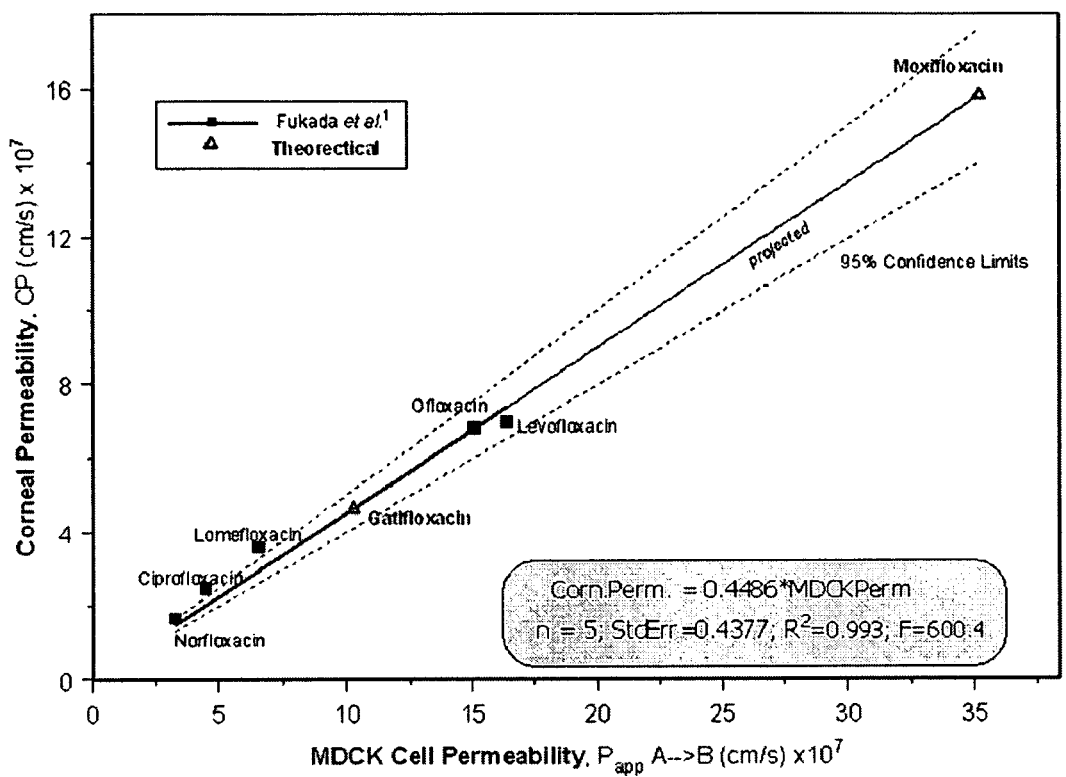

USE OF MDCK CELL LINE TO PREDICT CORNEAL PENETRATION OF DRUGS

This application claims priority from U.S. Provisional Application Ser. No. 60/564,790 filed on Apr. 23, 2004.

BACKGROUND OF THE INVENTION

Although there are a large number of agents that inhibit microbial infections in culture or even when administered systemically, many of these agents are not effective when administered via topical ocular application as a result of inadequate penetration of the drug through the cornea. Even within a structural class the observed in vivo activity of a compound depends on both the anti-microbial activity and the ability of the compound to localize at the appropriate concentration in the affected tissue. The present invention is directed to the discovery of physical properties that control the topical ocular activity of drugs (e.g., fluoroquinolone antibiotics), as well as to the provision of a method for identifying compounds that have sufficient corneal penetration capability to be administered via topical application to the eye.

The single cellular epithelial layer of the cornea is the primary barrier to the trans-corneal penetration of drug molecules. Although a number of methods have been used to enhance penetration across the corneal epithelium, these methods tend to disrupt the intercellular connections that serve as a defensive barrier protecting the eye from invasions by pathogens. Disruptions in this barrier often result in toxicity which is amplified upon repeated application.

A superior approach is to enhance trans-celluar penetration by designing or identifying compounds with optimum physical properties. Compounds in solution or suspension need to partition from the topical formulation into the lipid rich cellular membrane of the corneal epithelium, traverse the cell and exit through the basolateral epithelial cell membrane. As long as the formulation is in contact with the exterior surface of the eye, the steep concentration gradient serves as the driving force for penetration into the cornea. In this limited time, the physical properties of the molecule in the formulation govern the rate of drug penetration into and through the corneal epithelium.

Aqueous solubility and lipophilicity are two factors that govern the rate a drug penetrates the cornea (FIG. 1). However, other physical properties of the drug molecule (e.g., pKa and distribution coefficient) may also have an impact on corneal permeability.

For most topical ocular drugs, the rate-limiting barrier to corneal penetration is the two top cell layers of the corneal epithelium which are lipoidal in nature (FIG. 1B). A drug's lipophilicity is estimated by its octanol/water partition coefficient, $k_{oc}$, though the logarithm of this value, log P, is more often reported. If one takes into consideration the pH of the aqueous phase, the proportion of drug in its non-ionized or preferentially absorbed form can be determined, along with the distribution coefficient, or DC (Table 1). Due to the tri-laminate structure of the corneal membrane which effectively blocks passive diffusion by most molecules, the optimal n-octanol/water log P range for transcellular corneal drug penetration is 2-3.[16]

The pioneering work of Schoenwald found that corneal permeability is a function of lipophilicity for steroids[17] and β-blockers.[18] However, Wu et al.[19] found no such correlation for a small set of cephalosporins. Both, Fukada et al.[1] and Liu et al.[20] demonstrated that corneal permeability correlates with fluoroquinolone lipophilicity. Also Ruiz-Garcia et al.[21] observed that lipophilicity is the main factor governing intestinal fluoroquinolone absorption.

Several studies examining the tear concentrations and corneal penetration properties of fluoroquinolone antibiotics have been published.[8-11] However, only a limited amount of information has been published regarding the corneal penetration properties of the new fourth-generation fluoroquinolones, moxifloxacin and gatifloxacin. The present inventors conducted a study to (i) investigate the physical properties underlying the superior corneal penetration of moxifloxacin and (ii) develop a method for predicting the corneal permeability of moxifloxacin and other fluoroquinolones using in vitro data and mathematical models. This work resulted in the development of a new and more reliable method for predicting the corneal penetration of drug molecules.

A principal objective of the present invention is to provide a method for identifying drug molecules having the physical properties required for significant levels of corneal penetration.

A further objective of the present invention is to provide a method for differentiating or ranking drug molecules within a specified class (e.g., fluoroquinolones) based on the abilities of the individual molecules to penetrate the cornea.

SUMMARY OF THE INVENTION

The present invention is based on the discovery that corneal penetration of drug molecules is highly predicted by the permeation rate of the molecules in MDCK (Madin-Darby Canine Kidney) cells. In addition, permeability in the MDCK cell line can be predicted by the experimentally determined distribution coefficient described herein.

The above-cited discoveries resulted from a study of the corneal penetration characteristics of moxifloxacin and other fluoroquinolones. The study, which is discussed in greater detail below, demonstrated that the MDCK permeability values for moxifloxacin and other fluoroquinolones tested correlate very closely with actual in vivo corneal penetration values for these drug molecules. Moreover, the study showed that the physical properties that have typically been used in the past to predict corneal permeability (e.g., lipophilicity, aqueous solubility, pKa and distribution coefficient) are considerably less accurate than the method of the present invention.

BRIEF DESCRIPTION OF THE DRAWINGS

FIG. 1 is a two-part schematic illustration of factors that influence the ability of molecules to penetrate the corneal epithelium; and FIG. 2 is a graph showing the correlation between predicted corneal penetration values determined in accordance with the method of the present invention and actual corneal penetration rates.

DETAILED DESCRIPTION OF THE INVENTION

The present invention is directed to the use of a new in vitro model for evaluating the ability of a drug molecule to penetrate the cornea. The model involves the use of MDCK cell permeability values to predict the ability of drug molecules to penetrate the cornea. The MDCK permeability values of drug molecules can be determined by means of known methods, such as the methods described in the following scientific articles:

1. Horio, M, Pastan, I, Gottesman, M M, and Handler, J S. Transepithelial transport of vinblastine by kidney-derived cell lines. Application of a new kinetic model to estimate in situ $K_m$ of the pump. *Biochim.Biophys.Acta* 1027:116-122, 1990; and
2. Pan, B F, Dutt, A, and Nelson, J A. Enhanced transepithelial flux of cimetidine by Madin-Darby canine kidney cells overexpressing human P-glycoprotein. *J.Pharmacol.Exp.Ther.* 270:1-7, 1994.

The entire contents of the above-cited references relating to methods for determining MDCK permeation values for drug molecules are hereby incorporated in the present specification by reference. Such methods are further illustrated in Example 1 below. Various commercial scientific laboratories may be utilized to obtain MDCK permeation values (e.g., Absorption Systems, Exton, Pa., USA).

The method of the present invention comprises the following steps: (1) determining the MDCK permeation value for a drug molecule; and (2) entering said value in a suitable linear or quadratic statistical model to calculate a predicted corneal permeability value for said molecule. The statistical model is created by obtaining MDCK permeation values and corneal penetration values for at least two representative drug molecules, plotting those values on a graph and deriving a linear or quadratic statistical model from the graph. The following equation, which was derived from the data presented in Table 2 below, is an example of a statistical model of the type mentioned above:

Corneal Permeability=5.41(MDCK Permeability)−0.01(MDCK Permeability)$^2$

As further illustrated below, the predicted corneal permeation value can then be compared with the predicted values of other molecules for which actual in vivo corneal penetration data are available. This comparison provides a basis for assessing the potential corneal permeability of a drug molecule prior to actual testing in in vivo or ex vivo animal models.

The above-described method of predicting corneal permeability provides a means for evaluating large numbers of drug molecules, relative to the potential ability to administer the compounds via topical application to the eye, without performing expensive and time-consuming tests in in vivo and/or ex vivo corneal penetration models. The method is therefore quite valuable in screening drug molecules for possible utility in the ophthalmic field, as well as in structure-activity relationship ("SAR") studies directed to identification of the most efficacious compounds within a specified genus or class.

The methods of the present invention are described in greater detail below relative to research conducted with a specific class of drug molecules, i.e., fluoroquinolone antibiotics. However, the ability of the methods to predict corneal penetration is not limited to this class of drugs. Rather, the methods are broadly applicable to all types and classes of drugs.

Fluoroquinolone antibiotics have become the treatment of choice for ocular infections in recent years. Currently, seven fluoroquinolones have been approved for ophthalmic use namely, norfloxacin, ofloxacin, lomefloxacin, levofloxacin, ciprofloxacin, and more recently gatifloxacin and moxifloxacin. The structures of these compounds are shown below:

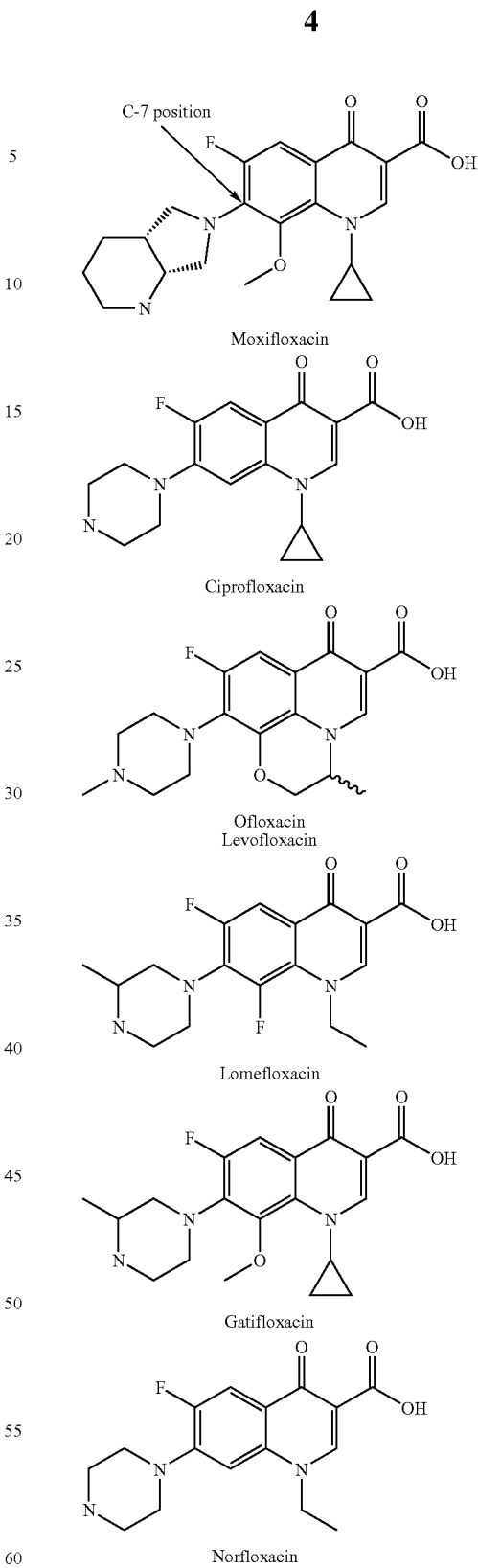

These antibiotics possess excellent activity against a wide range of bacteria[3-6] and act by interfering with DNA gyrase (topoisomerase II) and topoisomerase IV.[7] Both are key enzymes involved in DNA replication. Fourth-generation fluoroquinolones such as moxifloxacin are more balanced in their inhibition of these two enzymes making them less likely to develop resistant strains. Moxifloxacin also contains a bulky C-7 substituent that causes it to be a poor substrate for bacterial efflux pumps and effectively prevents it from being removed from the bacterial cell.[7] Thus, more of the antibiotic accumulates within the bacterial cell resulting in more rapid cell death.

The above-described method for predicting corneal permeability was utilized to calculate the predicted corneal penetration capabilities of moxifloxacin and other fluoroquinolones. The physical properties of the compounds (e.g., aqueous solubility, lipophilicity, etc.) were also determined. The procedures utilized are described in Example 1, below.

In order to determine if the predicted corneal penetration values determined by the above-described method accurately reflect the actual corneal penetration properties of moxifloxacin and other fluoroquinolones, an ex vivo corneal penetration study in a rabbit model was conducted. The procedures utilized in that study are described in Example 2, below.

EXAMPLE 1

Determination of MDCK Values and Other Properties

Materials

Moxifloxacin, gatifloxacin, ciprofloxacin, lomefloxacin, levofloxacin, ofloxacin and norfloxacin were purchased in 100 mg quantities from Sequoia Research Products Ltd, UK.

Methods

In vitro MDCK cell permeability. Permeability and transport studies were conducted and the data were analyzed at Absorption Systems, Exton, Pa., using methods previously described.[12,13] MDCK(MDR) monolayers were grown to confluence on collagen-coated, microporous, polycarbonate membranes in 12-well Costar Transwell plates. To ensure monolayer integrity, the trans epithelial electrical resistance (TEER) was measured. Cell monolayers with TEER values>1900 $\Omega \cdot cm^2$ were used for these transport studies. The permeability assay buffer was Hank's Balanced Salt Solution containing 10 mM HEPES and 15 mM glucose at a pH of 7.0-7.2. Permeability through a cell-free (blank) membrane was studied to determine non-specific binding and free diffusion of the test article through the device. Dosing solution concentrations of the test articles were 10 μM in assay buffer. At each time point, 1 and 2 hours, a 200-μL aliquot was taken from the receiver chamber and replaced with fresh assay buffer. Cells were dosed on the apical side [apical-to-basolateral, absorptive transport, (B-A)] or basolateral side [basolateral-to-apical, secretory transport, (B-A)] and incubated at 37° C. with 5% $CO_2$ and 90% relative humidity. Each determination was performed in duplicate. Lucifer Yellow permeability was measured for each monolayer after the experiment, to ensure that the cell monolayer integrity and viability was not compromised by the test article. Post experiment Lucifer Yellow permeability in monolayers was between $0.24-0.75 \times 10^{-6}$ cm/s.

To determine the transport of compounds in the absence of functional P-gp activity, the above experimental conditions were used but in the presence of the P-gp inhibitor cyclosporin A (CSA).[14] For the studies using CSA, cells were pre-incubated for 30 minutes with the inhibitor (10 μM) and washed; during the permeation determination period CSA (10 μM) was present on both sides of the membrane. The $P_{app}$ A-B determined in the presence of CSA was taken as an estimate of the permeability attributed to passive diffusion for the compound ($P_{app\ PD}$).

Aqueous solubility determination. The compound of interest was added to 0.1M phosphate buffer at pH 7.4 and the pH was adjusted as desired. Samples containing an excess of un-dissolved material were stirred at ambient temperature for a minimum of 18 hours. Sample pH was adjusted as required and the mixture stirred an additional 15 minutes and filtered through a 0.45 micron nylon filter. The filtrate was analyzed by RP-HPLC against concentration standards for the compound of interest.

Distribution coefficient determination. Partitioning of compounds between n-octanol and aqueous buffer was determined at pH 5.0 and pH 7.4 using 0.1M acetate and 0.1M phosphate buffer respectively. The initial concentration ($C_1$) of compound in buffer and the buffer concentration following extraction with n-octanol ($C_2$) were determined by RP-HPLC analysis against concentration standards for the specific compound. The distribution coefficient (DC) of a compound at a given pH was calculated using the equation $DC_{pH}=(C_1-C_2)/C_2$.

$pK_a$ determination. Ionization constants were determined by potentiometric titration (Kyoto AT-310 Potentiometric Titrator) in water or a mixture of water and an organic solvent such as methanol, acetone, or acetonitrile. If a solvent mixture was used, the nominal $pK_a$ values were plotted against the percentage of organic solvent to provide by extrapolation the $pK_a$ of the compound in water.

Computed properties. a log P, aMR and C-7 π values were computed using the Ghose algorithm.[2] The $\log(DC_{7.0})$ values were computed using the log(DC) module from Advanced Chemical Development.[15] The results of the calculations are shown in Table 1 below.

EXAMPLE 2

Ex-Vivo Corneal Penetration

Rabbits were sacrificed by first anaesthetizing with ketamine (30 mg/Kg) and xylazine (6 mg/Kg) followed by an injection of an overdose of SLEEPAWAY® (sodium pentobarbital, 1 ml of a 26% solution) into the marginal ear vein. The intact eyes, along with the lids and conjunctival sacs were then enucleated and immediately stored in about 70 ml of fresh BSS PLUS® Sterile Irrigating Solution (Alcon Laboratories, Inc.) saturated with $O_2/CO_2$ (95:5). Within one hour, corneas were mounted in the modified perfusion chamber as described by Schoenwald and Huang (G1). BSS PLUS® solution was used as the receiving and rinsing solution throughout the perfusion experiments. Steady-state conditions were used in order to determine the apparent permeability coefficients. After mounting the corneas in the chamber, 7.5 mls of BSS PLUS® solution was added to the receiving chamber (endothelial side of the cornea). Then, 7 mls of 0.1 mMole solutions of each fluoroquinolone prepared in BSS PLUS® solution was added into the donor chamber (epithelial side of the cornea). Throughout the experiment, both solutions were bubbled continuously with $O_2/CO_2$ (95:5) at the rate of about one bubble per second. This provides mixing of the solution in each chamber, oxygenation of the cornea, and pH control. Samples (0.15 ml) were withdrawn from the receiving chamber at 30 min intervals over a period of five hours. BSS PLUS® solution (0.15 ml) was added back to the receiving chamber after each withdrawal to compensate for loss of volume.

At the end of each permeability experiment, The final volume of the receiving chambers was noted, and the viability of the corneas was assessed by determining their hydration level: The corneas were trimmed of excess scleral tissue and conjunctiva, blotted, weighed, dried overnight at room temperature under vacuum over phosphorus pentoxide, and then re-weighed. All corneas were found to have the normal hydration level of 76-80%.

The apparent permeability coefficients ($P_{app}$, cm/sec) were determined by means of the following equation:

$$P_{app} = \text{rate}/(60 \times A \times C)$$

wherein the rate is the steady state accumulation of glucocorticoid in the receiving chamber in units of µg/min; A is the corneal surface area, exposed within the chambers, in units of cm² — a value of 1.087 cm² was used in the calculations; C is the steady state measured concentration of glucocorticoid in the donor solution in units of µg/ml or ppm; and 60 is the conversion of minutes to seconds. The results are shown in Table 1.

TABLE 1

Experimentally Determined Molecular Properties.

| Compound | Aqueous Solubility (%) | $DC_{7.4}$ | $\log(DC_{7.4})$ | MDCK Permeability (cm/s) × $10^7$ | Corneal Permeability (cm/s) × $10^7$ | $pKa_1$ | $pKa_2$ |
|---|---|---|---|---|---|---|---|
| Ofloxacin | 0.35 | 0.37 | −0.44 | 15.1 | 50 | 6.25 | 8.38 |
| Ciprofloxacin | 0.02 | 0.03 | −1.51 | 4.5 | 18.2 | 6.22 | 8.60 |
| Norfloxacin | 0.05 | 0.03 | −1.60 | 3.3 | 22 | 6.34 | 8.63 |
| Moxifloxacin | >6.43 | 0.61 | −0.22 | 35.2 | 91 | 6.31 | 9.30 |
| Levofloxacin | <1.85 | 0.36 | −0.45 | 16.4 | 29 | 6.34 | 8.41 |
| Gatifloxacin | 0.21 | 0.11 | −0.97 | 10.3 | 25 | 6.23 | 8.93 |
| Lomefloxacin | 0.13 | 0.04 | −1.45 | 6.6 | 35 | 6.05 | 9.00 |

The following equation was utilized to mathematically relate the ex vivo rabbit corneal permeability rates determined via the testing described in Example 2 with MDCK cell permeability rates calculated via the work described in Example 1:

Corneal Permeability=2.65(MDCK Permeability)
$n=7$; $sd=11.80$; $R^2=0.9415$; $F_{1,4}=96.51$;
$p<0.0001$ wherein $R^2$ is the correlation coefficient, sd is the standard error, and F, is the F-statistic. It was determined that there is a very strong correlation ($R^2=0.94$) between the MDCK and rabbit values, as shown in FIG. 2.

The MDCK permeability values determined as a result of the testing described in Example 1 were converted to predicted corneal permeability values pursuant to the procedure described above, utilizing the equation:

Corneal Permeability=5.41(MDCK Permeability)−
0.01(MDCK Permeability)²

A side-by-side comparison of the corneal permeability values predicted based on the method of the present invention and the actual corneal permeability values determined as a result of the ex vivo testing described in Example 2 is presented in Table 2, below:

TABLE 2

Comparison of Predicted and Actual Corneal Permeability Values

| Compound Name | MDCK-MRD1 Permeability, Papp nm/s | MDCK² | Ex vivo Rabbit Corneal Permeability, Papp nm/s | Predicted Corneal Permeability |
|---|---|---|---|---|
| Buspirone | 325 | 105625 | 665 | 675.82 |
| Apraclonidine | 3.8 | 14.44 | 38 | 19.58 |
| Fluorescein | 6.6 | 43.56 | 160 | 33.83 |
| Pilocarpine | 36.8 | 1354.24 | 98 | 177.99 |
| Nepafenac | 181 | 32761 | 740 | 625.74 |
| Timolol | 33.9 | 1149.21 | 240 | 164.91 |
| Atenolol | 1.4 | 1.96 | 21 | 7.25 |
| Betaxolol | 202 | 40804 | 600 | 657.76 |
| Dexamethasone | 37.8 | 1428.84 | 92 | 182.47 |
| Moxifloxacin | 35.2 | 1239.04 | 91 | 170.79 |
| Ciprofloxacin | 4.5 | 20.25 | 22.5 | 23.16 |

This comparison demonstrates that the method of the present invention provides a very accurate means for predicting corneal penetration of drug molecules.

Table 2 includes values for several compounds other than the fluoroquinolones identified in Example 1. These values were determined by means of the same methodology utilized for the fluoroquinolones. A comparison of the predicted and actual corneal penetration values for these compounds demonstrates that the method of the present invention is useful as a means for predicting the corneal penetration of drug molecules other than fluoroquinolones.

REFERENCES

1. Fukada, M and Sasaki. K In vitro topically applied fluoroquinolone penetration into the anterior chamber. Nippon Ganka Gakkai Sasshi 99:532-536, 1995.
2. Viswanadhan, V N, Ghose, A K, Revankar, G R, Robins, R K. Atomic physicochemical parameters for three dimensional structure directed quantitative structure-activity relationships. 4. Additional parameters for hydrophobic and dispersive interactions and their application for an automated superposition of certain naturally occurring nucleoside antibiotics. *J. Chem. Inf. Comp. Sci.,* 29:163-172, 1989.
3. Kowalski, R P, Dhaliwal, D K, Karenchak, L M, Romanoswski, E G, Mah, F S, Ritterband, D C, and Gordon, Y J. Gatifloxacin and moxifloxacin: an in vitro susceptibility comparison to levofloxacin, ciprofloxacin, and ofloxacin using bacterial keratitis isolates. *Am. J. Ophthalmol.* 136: 500-505, 2003.
4. Romanowski, E G, Kowalski, R P, Yates, K A, Mah, F S, and Gordon, Y J. The in vitro evaluation of the ophthalmic fluoroquinolones against bacterial conjunctivitis isolates. *Presented at the Ocular Microbiology and Immunology Group Meeting,* Anaheim, Calif., Nov. 15, 2003.
5. Caballero, A R, Thibodeaux, B A, Dajcs, J J, Marquart, M E, Johnston, K H, Bush, J T, and O'Callaghan, R J. *Presented at the Ocular Microbiology and Immunology Group Meeting,* Anaheim, Calif., Nov. 15, 2003.
6. Mather, R, Karenchak, L M, Romanowski, E G, and Kowalski, R P. Fourth generation fluoroquinolones: new weapons in the arsenal of ophthalmic antibiotics. *Am. J. Ophthalmol.* 133:463-466, 2002.
7. Pestova, E, Millichap, J J, Noskin, G A, Peterson, L R. Intracellular targets of moxifloxacin: a comparison with other fluoroquinolones. *J. Antimicrob. Chemother.* 45:583-590, 2000.
8. Robertson, S M, Sanders, M, Jasheway, D, Trawisck, D, Veltman, J, Hamner, S, Schlech, B A, Hilaski, R, and Dahlin, D C. Penetration and distribution of moxifloxacin and ofloxacin into ocular tissues and plasma following topical ocular administration to pigmented rabbits. *Presented at the 75$^{th}$ Annual Meeting of the Association for Research in Vision and Ophthalmology,* May 11-15, 2003 Fort Lauderdale, Fla.
9. Katz, H R, Masket, S, Lane, S S, Sail, K, Orr, S C, BcCue, B A, Faulkner, R D, Dahlin, D C. Human aqueous humor penetration pharmacokenetics of moxifloxacin after topical administration of moxifloxacin 0.5% ophthalmic solution. *Presented at the Ocular Microbiology and Immunology Group Meeting, Anaheim, Calif.,* Nov. 15, 2003.
10. Kim A S, McCulley, J P, Cavanagh, H D, Jester, J V, Bugde, A C, Kovoor, T, Petroll, W M. Evaluation of the effects of topical ophthalmic fluoroquinolones on the cornea using in vivo confocal microscopy. *Presented at the 75$^{th}$ Annual Meeting of the Association for Research in Vision and Ophthalmology,* May 11-15, 2003 Fort Lauderdale, Fla.
11. Jester, J V, Petroll, W M, Bean, J, Parker, R D, Carr, G J, Cavanagh, H D, Maurer, J K. Area and depth of surfactant-induced corneal injury predicts extent of subsequent ocular responses. *Invest. Ophthalmol. Vis. Sci.* 39: 2610-2625, 1998.
12. Horio, M, Pastan, I, Gottesman, M M, and Handler, J S. Transepithelial transport of vinblastine by kidney-derived cell lines. Application of a new kinetic model to estimate in situ $K_m$ of the pump. *Biochim. Biophys. Acta* 1027: 116-122, 1990.
13. Pan, B F, Dutt, A, and Nelson, J A. Enhanced transepithelial flux of cimetidine by Madin-Darby canine kidney cells overexpressing human P-glycoprotein. *J. Pharmacol. Exp. Ther.* 270:1-7, 1994.
14. Arimori, K, Kuroki, N, Hidaka, M, Iwakiri, T, Yamsaki, K, Okumura, M, Ono, H, Takamura, Kikuchi, M, and Nakano, M. Effect of P-glycoprotein modulator, cyclosporin A, on the gastrointestinal excretion of irinotecan and its metabolite SN-38 in rats. *Pharm. Res.* 20:910-917, 2003.
15. Calculated using the log(DC) module. Advanced Chemistry Development (ACD) Software Solaris V4.67 (2004).
16. Lee, V H, and Bundgaard, H. Improved Ocular Drug Delivery with Prodrugs, in *Prodrugs. Topical and Ocular Drug Delivery.* Sloan, K. B. (ed.), p221-297, Marcel Dekker, New York, N.Y., 1992.
17. Schoenwald R D, Ward R L. Relationship between steroid permeability across excised rabbit cornea and octanol-water partition coefficients. *J Pharm Sci.* 67(6): 786-8, 1978.
18. Schoenwald R D, Huang H S. Corneal penetration behavior of beta-blocking agents I: Physiochemical factors. *J Pharm Sci.* 72(11):1266-72, 1983.
19. Wu, C-Y, Chiang, C-H, Huang, H-S. In vitro corneal permeability of cephalosporins. *Chin. Pharm. J.* 43(3): 230-235, 1991.
20. Liu, W, Liu, Q F, Perkins, R, Drusano, F, Louie, A, Madu, A, Mian, U, Mayers, M and Miller, M H. Pharmacokinetics of Sparfloxacin in the Serum and Vitreous Humor of Rabbits: Physicochemical Properties that Regulate Penetration of Quinolone Antimicrobials. *Antimicrobial Agents and Chemotherapy June:* 1417-1423, 1998.
21. Ruiz-Garcia, A, Sanchez-Castano, G, Freixas, J, Bermejo, M, Merino, V, Garrigues, T M, Pla-Delfina, J M, Biophysical models in drug development: 6-fluoroquinolone derivatives. *Proceedings of the International Symposium on Controlled Release of Bioactive Materials.* 27$^{th}$:708-709, 2000.
22. Gonzalez-Mariscal, L, Chavez de Ramirez B, and Cereijido, M. Tight junction formation in cultured epithelial cells (MDCK). *J. Membrane Biol.* 86(2):113-125, 1985.
23. Owen G, Dembinska O, Stout K R, Mendiola M K. Corneal penetration and changes in corneal permeability of moxifloxacin versus gatifloxacin. *Presented at the 76$^{th}$ Annual Meeting of the Association for Research in Vision and Ophthalmology,* Apr. 25-29, Fort Lauderdale, Fla., 2004.
24. Prausnitz, M R, and Noonan, J S, Permeability of cornea, sclera and conjunctiva: A literature analysis for drug delivery to the eye. *J. Pharm. Sci.* 87(12): 1479-1488, 1998.
25. Fu, X C, Liang, W Q, Preidiction of corneal permeability using polar molecular surface areas. *Pharmazie,* 56:667, 2001.
26. Fu, X C, Liang, W Q, A simple model for the prediction of corneal permeability. *Intl. J. Pharm.* 232:193-197, 2002.
27. Clark, D E. Rapid calculation of polar molecular surface area and its application to the prediction of transport phenomena. 1. Prediction of intestinal absorption. J. Pharm. Sci. 88(8): 807-814, 1999.

We claim:

1. An in vitro method of evaluating the corneal permeability of a drug molecule, which comprises determining the permeation rate of the molecule in MDCK cells and converting said permeation rate to a predicted corneal penetration rate by means of a suitable quadratic equation.

2. A method of screening drug molecules for potential use in treating one or more ophthalmic conditions via topical ocular application of said molecules, wherein the method of claim 1 is utilized to identify drug molecules that are capable of penetrating the cornea at therapeutic levels.

3. A method according to claim 1, wherein said permeation rate of the molecule is converted to said predicted corneal penetration rate by means of the following equation, where MDCK Permeability is in nm/s:

$$\text{Corneal Permeability} = 5.41(\text{MDCK Permeability}) - 0.01(\text{MDCK Permeability})^2.$$

* * * * *